US00PP37273P2

(12) United States Plant Patent
Marczynski

(10) Patent No.: US PP37,273 P2
(45) Date of Patent: Feb. 17, 2026

(54) CLEMATIS PLANT NAMED 'Violet Lampion'

(50) Latin Name: ***Clematis* spp.**
Varietal Denomination: Violet Lampion

(71) Applicant: Spring Meadow Nursery, Grand Havem, MI (US)

(72) Inventor: Szczepan Marczynski, Pruszkow (PL)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 18/809,077

(22) Filed: Aug. 19, 2024

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
CPC ..... A01H 5/02; A01H 5/00; A01H 6/72
See application file for complete search history.

(56) References Cited

PUBLICATIONS

Zielony Showroom Plant News 2023 retrieved on Jul. 14, 2025 at https://www.zielonyshowroom.pl/nowosci-2023/, 8 pp. (Year: 2023).*
Zrodlo Dobrych Pnaczy Clematis New Introductions, retrieved on Jul. 14, 2025 at https://www.clematis.com.pl/en/wholesale-offer2/new-introductions/, 9 pp. (Year: 2025).*

* cited by examiner

*Primary Examiner* — June Hwu

(57) ABSTRACT

A new and distinct cultivar of *Clematis* spp. plant named 'Violet Lampion' is described, characterized by large, abundant purple flowers with two blooming seasons. Flowers produce durable seed heads with an attractive "fluffy" appearance. The new variety is a *Clematis*, normally used as an ornamental garden or landscape plant.

4 Drawing Sheets

Figure 1:
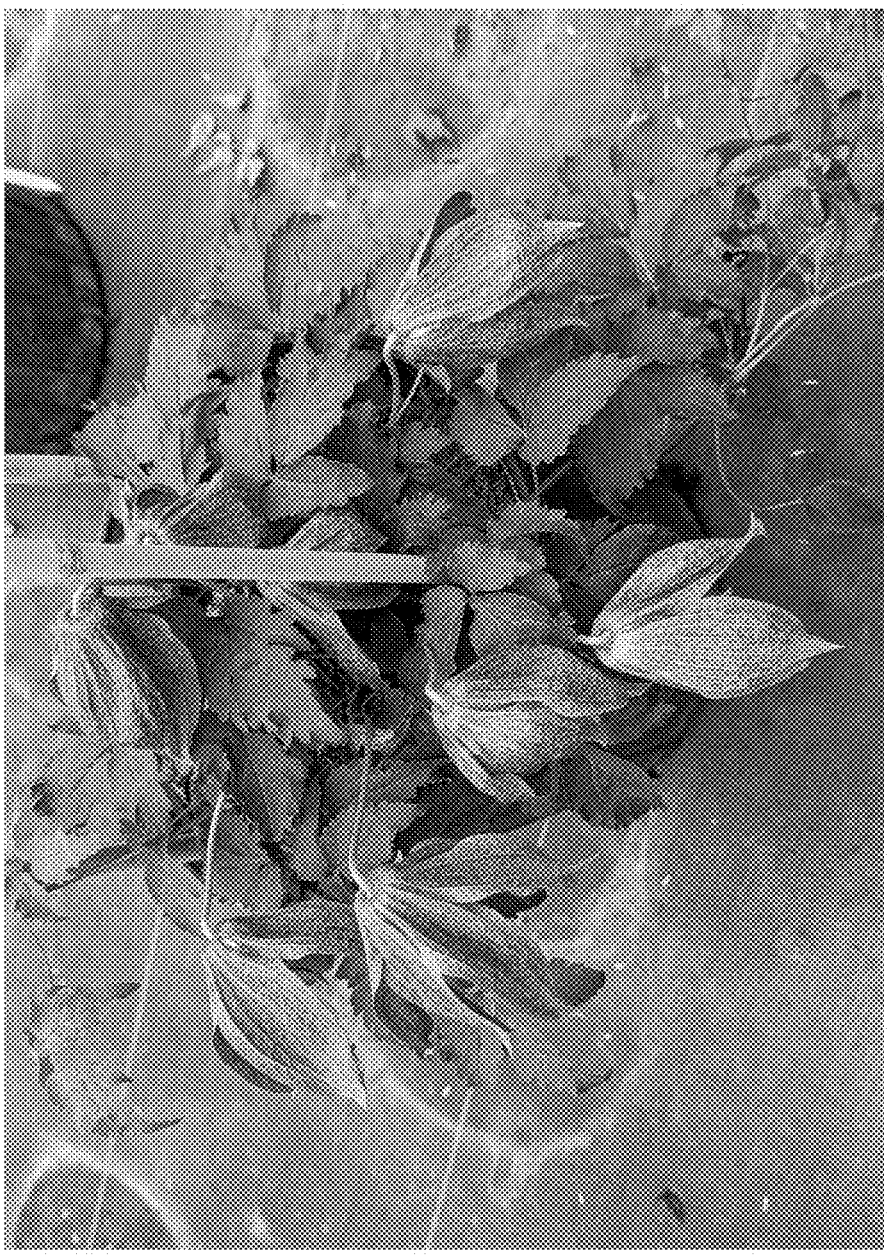

Latin name of the genus and species: *Clematis* spp.
Variety denomination: 'VIOLET LAMPION'.

BACKGROUND OF THE INVENTION

The new cultivar is the product of a planned breeding program by the inventor to produce new *Clematis* cultivars with large flowers in different colors. 'Violet Lampion' is the result of the crossing of the seed parent, *Clematis* (*faurei* x *sibirica*) x *macropetala* 'Joe Zary', unpatented, and the pollen parent, *Clematis alpina* 'Purple Spider', unpatented. The crossing was made in May 2015 at a nursery in Pruszków, Poland. 'Violet Lampion' was found and selected at the same location by the inventor in May 2016.

The first asexual reproduction was performed in June 2016 by softwood cuttings at the same nursery in Pruszków, Poland. *Clematis* 'Violet Lampion' has been found to retain its distinctive characteristics through successive asexual propagations.

SUMMARY OF THE INVENTION

The cultivar 'Violet Lampion' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Violet Lampion' These characteristics in combination distinguish 'Violet Lampion' as a new and distinct *Clematis* cultivar:

1. Larger flowers than any other *Clematis alpina* currently on the market.

2. Medium purple flowers with a drooping/nodding aspect.
3. Abundant flowers with two flowering seasons in April-May and July-August.
4. Irregularly toothed dark green leaves.
5. Durable seed heads with an attractive fuzzy/fluffy appearance.

PARENT COMPARISONS

Plants of the new cultivar 'Violet Lampion' are comparable to the seed parent in most horticultural characteristics; however, the new variety 'Violet Lampion' differs in the following:

1. Flowers of the new variety are larger than the flowers of the seed parent.
2. Flowers of the new variety are single, while flowers of the seed parent are semi-double.
3. Leaf margins of the new variety are irregularly toothed, while leaves leaf margins of the seed parent are non-distinct entire.
4. Seed heads of the new variety are fluffy and durable, while the seed heads of the seed parent are small and non-ornamental.

Plants of the new cultivar 'Violet Lampion' are comparable to the pollen parent in most horticultural characteristics; however, the new variety 'Violet Lampion' differs in the following:

1. Flowers of the new variety are larger than the flowers of the pollen parent.
2. Flowers of the new variety are single, while flowers of the pollen parent are semi-double.

3 . Flower color of the new variety is medium purple, while the flower color of the pollen parent is very dark purple.

COMMERCIAL COMPARISON

Plants of the new cultivar 'Violet Lampion' are comparable to the commercial variety *Clematis alpina* 'Blue Dancer', unpatented. The two *Clematis* varieties are similar in most horticultural characteristics; however, the new variety 'Violet Lampion' differs in the following:

1. Petals of the new variety are broader, with smaller gaps in between, while petals of this comparator are narrower, with larger gaps.
2. Flowers of the new variety are larger than flowers of this comparator.

BRIEF DESCRIPTION OF THE PHOTOGRAPHS

The accompanying photograph in FIG. 1 illustrates in full color a typical plant of 'Violet Lampion' grown in a poly-greenhouse in Grand Haven, Michigan. This plant is approximately 2-3 years old, grown in a 3-gallon container.

Figure 2:
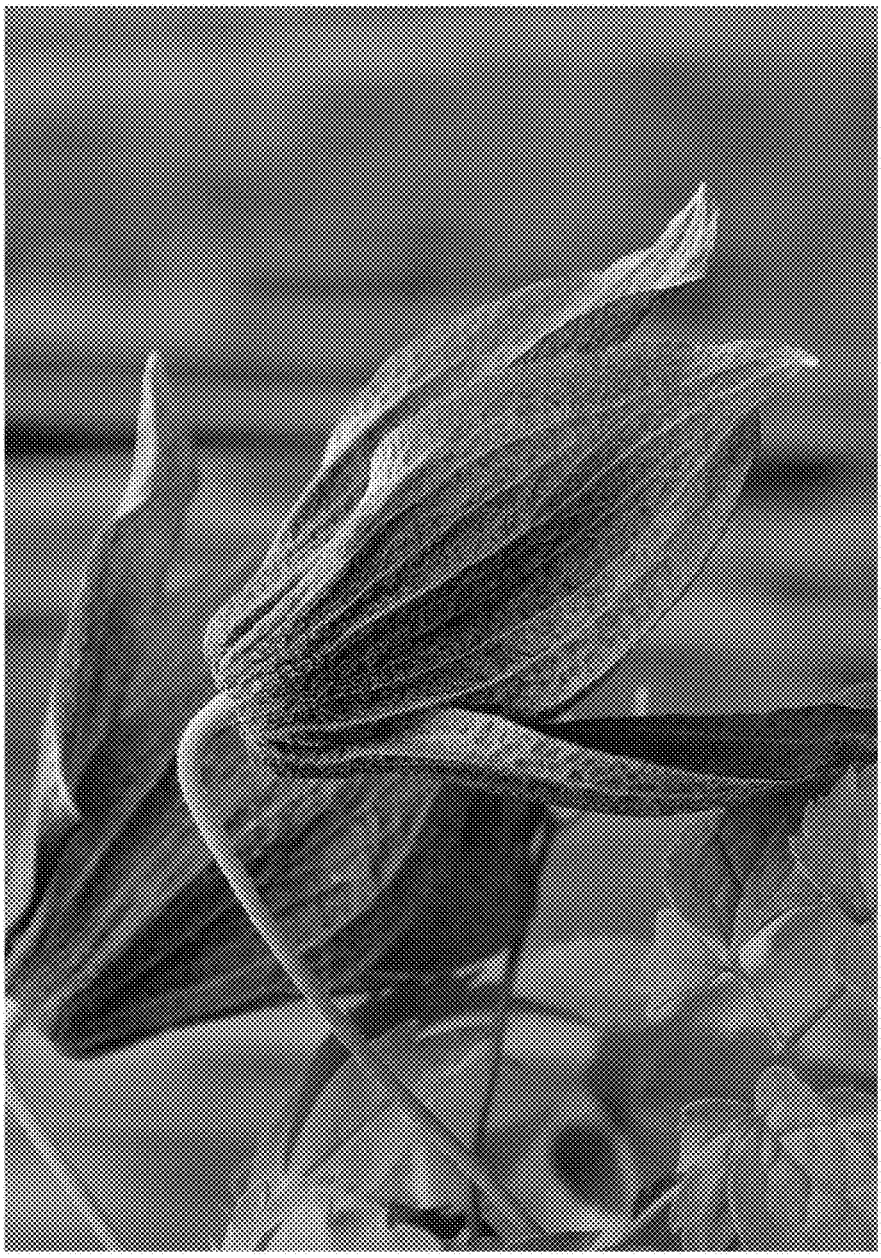

FIG. 2 illustrates in full color a close-up of the underside of two flowers of 'Violet Lampion'.

Figure 3:
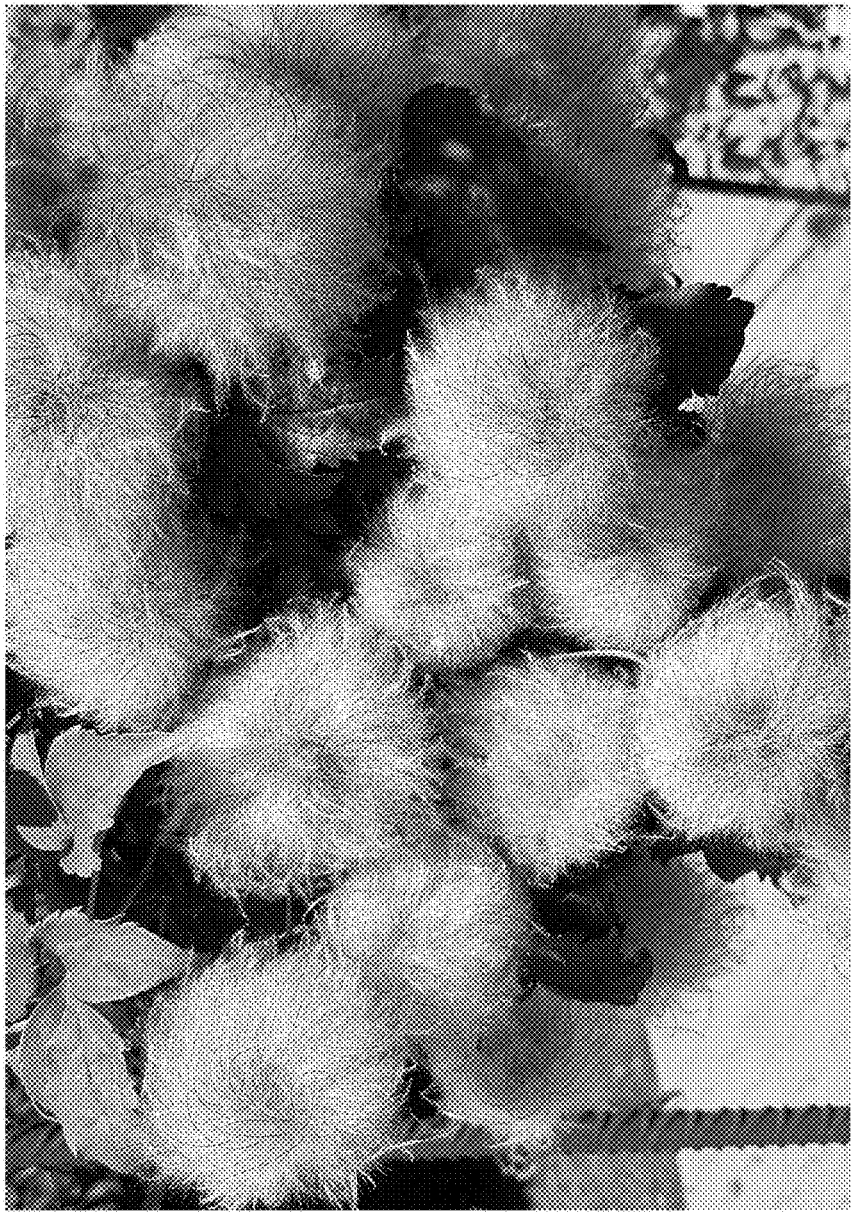

FIG. 3. is a photograph of the seed heads.

Figure 4:
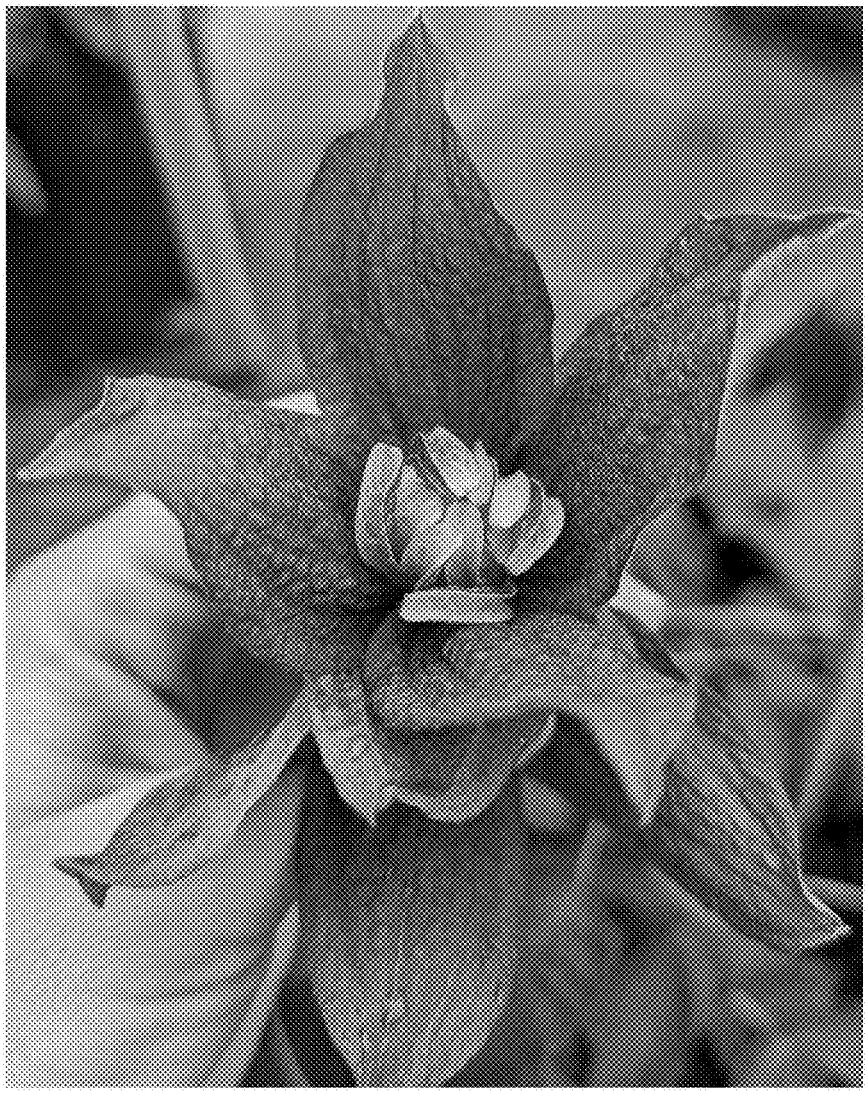

FIG. 4 is a photograph of a mature flower, showing the upper side of the flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'Violet Lampion' plants grown in a poly-greenhouse in Grand Haven, Michigan. The plants were about 2 to 3 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Clematis* spp. 'VIOLET LAMPION'.

PROPAGATION

Type of propagation typically used: Softwood cuttings.

PLANT

Age of plant described: 2 to 3 years.
Plant type: Flowering vine.
Growth habit: Upwards and outwards in a vining, climbing, or sprawling manner.
Growth rate: Fast.
Vigor: Highly vigorous.
Plant spread: 100 cm.
Plant height: 40 cm.
Stem:
- *Branching habit.*—Freely branching.
- *Number of lateral branches.*—About 10.
- *Shape.*—Round.
- *Color.*—New Growth: RHS Yellow-Green 144A. Old Growth (Bark): RHS Greyed-Orange 166A.
- *Length.*—90 cm.
- *Width.*—3 mm.
- *Aspect.*—0° to 90° relative to the ground, depending upon staking/trellising.
- *Strength.*—Strong, with new growth being somewhat flexible and old growth being rigid.
- *Pubescence.*—Very fine, sparse hairs on new growth only.
- *Internode length.*—12 cm.

FOLIAGE

Leaf:
- *Arrangement.*—Palmately trifoliate, compound.
- *Leaflet number.*—3 per leaf.
- *Length.*—Leaf: 12 cm. Leaflet: 9 cm.
- *Width.*—Leaf: 15 cm. Leaflet: 5 cm.
- *Leaflet shape.*—Ovate.
- *Leaflet apex.*—Caudate, with a tendency to curl abaxially.
- *Leaflet base.*—Terminal leaflet base rounded. Lateral leaflet base obtuse.
- *Leaflet margin.*—Irregularly toothed. Both shallowly crenate and shallowly dentate.
- *Leaflet texture.*—Upper Side: Glabrous and somewhat fleshy. Under Side: Glabrous and somewhat fleshy, with raised venation.
- *Color.*—Young foliage, upper side: RHS Yellow-Green 146A. Young foliage, under side: RHS Yellow-Green 147B. Mature foliage, upper side: RHS Yellow-Green 147A. Mature foliage, under side: RHS Yellow-Green 147B.
- *Pubescence.*—None.
- *Venation pattern.*—Palmate.
- *Venation color.*—Upper Side: RHS Yellow-Green 144A. Under Side: RHS Yellow-Green 144A.

Petiolule:
- *Length.*—1.5 cm.
- *Width.*—2 mm.
- *Color.*—Upper Side: RHS Yellow-Green 144A. Under Side: RHS Yellow-Green 144A.
- *Texture.*—Very lightly pubescent, both sides.

Petiole:
- *Length.*—4 to 8 cm.
- *Width.*—2 mm.
- *Color.*—Upper Side: RHS Yellow-Green 144A. Under Side: RHS Yellow-Green 144A.
- *Texture.*—Very lightly pubescent, both sides.

Other: Undersides of leaves have a shiny, somewhat lustrous quality.

FLOWER

Natural flowering season: April through May, with a lesser repeat blooming July through August.
Flower arrangement: Single rotate flowers along the lengths of lateral branches, but primarily at the terminal ends.
Flower form: Rotate.
Flowering habit: Flowering from leaf axils, primarily at the terminal ends of branches. Flowering occurs on both previous year's growth and current year's growth.
Flowers and buds per lateral stem: 2 to 5 flowers, and 1 to 2 buds.

Flowers and buds per plant: 50 to 100.
Fragrance: None.
Buds:
*Length.*—2 cm.
*Diameter.*—1.5 cm.
*Shape.*—Ovate.
*Color.*—RHS Yellow-Green 145B.
Flower:
*Shape.*—Campanulate.
*Length.*—8 to 12 cm.
*Diameter.*—8 to 12 cm.
*Depth.*—4 to 6 cm.
*Aspect.*—Drooping.
*Longevity.*—2 weeks on plant.
*Persistence.*—Self-cleaning.
Tepals:
*General appearance.*—Matte purple tepals on a downward-facing/drooping flower, collectively forming a cupped, bell shape.
*Arrangement.*—Whorl. Touching.
*Quantity.*—4 to 6.
*Fused.*—No.
*Shape.*—Elliptic.
*Apex.*—Acute to acuminate.
*Base.*—Blunt.
*Margin.*—Entire. Weakly undulate.
*Length.*—6 cm.
*Width.*—2.5 cm.
*Texture.*—Coriaceous, both sides.
*Color.*—When opening, upper side: RHS Violet 86A. When opening, under side: Near RHS Purple 79A, with Greyed-Purple N187B indumentum. Fully opened, upper side: RHS Violet 86A. Fully opened, under side: Near RHS Purple 79A, with Greyed-Purple N187B indumentum.
*Tepal venation.*—Pinnate. Lower surface colored near Violet 84C. Upper surface colored near Violet 83C.
Peduncle:
*Length.*—8 cm.
*Diameter.*—2 mm.
*Angle.*—Variable, though generally ending with a curve which is approximately 120° (25° below horizontal).
*Strength.*—Good.
*Texture.*—Very lightly pubescent.
*Color.*—RHS Yellow-Green 144A.
Staminodes:
*Quantity.*—Approximately 20.
*Length.*—3 cm.
*Width.*—3 mm.
*Color.*—RHS Yellow-Green 145D lower surface, Violet 86A upper surface.

REPRODUCTIVE ORGANS

Stamens:
*Number.*—About 80.
*Filament color.*—RHS Yellow-Green 145D.
Anther:
*Length.*—2 mm.
*Shape.*—Oblong.
*Color.*—RHS Yellow 4C.
*Pollen.*—Sparse.
*Pollen color.*—RHS Yellow 4D.
Pistil:
*Number.*—About 300.
*Length.*—1.2 cm.
Stigma:
*Shape.*—Filamentous.
*Color.*—RHS Yellow-Green 145D.
*Style length.*—1 cm.
*Style color.*—RHS Greyed-White 156C.
Ovary:
*Color.*—RHS Yellow-Green 145B.

SEEDS

*Quantity.*—About 300 achenes per seed head.
*Length.*—8 mm.
*Diameter.*—8 mm.
*Color.*—RHS Brown 200B.
*Other.*—Flowers produce achenes with long, hair-like "tails" which collectively form an attractive "pom-pom" like seed head (2 to 3 cm wide and long). Style length 1 cm, style color Greyed- White 156C.

OTHER CHARACTERISTICS

Disease resistance: Resistance or susceptibility to diseases or pests of *Clematis* not observed to date.
Temperature range: Tolerant to USDA zones 4 to 9.

What is claimed is:

1. A new and distinct cultivar of *Clematis* plant named 'VIOLET LAMPION' as herein illustrated and described.

* * * * *